(12) United States Patent
Amirav et al.

(10) Patent No.: US 8,591,630 B2
(45) Date of Patent: Nov. 26, 2013

(54) FAST GAS CHROMATOGRAPH METHOD AND DEVICE FOR ANALYZING A SAMPLE

(76) Inventors: Aviv Amirav, Hod Hasharon (IL); Alexander B. Fialkov, Tel Aviv (IL)

( * ) Notice: Subject to any disclaimer, the term of this patent is extended or adjusted under 35 U.S.C. 154(b) by 329 days.

(21) Appl. No.: 12/899,288

(22) Filed: Oct. 6, 2010

(65) Prior Publication Data
US 2012/0085148 A1   Apr. 12, 2012

(51) Int. Cl.
*B01D 53/02*   (2006.01)
(52) U.S. Cl.
USPC .......... 95/87; 95/82; 96/101; 96/103; 96/105; 96/106; 73/23.39
(58) Field of Classification Search
USPC .................. 95/82, 87; 96/101, 103, 105, 106; 73/23.35, 23.39, 23.42
See application file for complete search history.

(56) References Cited

U.S. PATENT DOCUMENTS

| | | | |
|---|---|---|---|
| 5,742,050 A * | 4/1998 | Amirav et al. | 250/288 |
| 5,808,178 A * | 9/1998 | Rounbehler et al. | 73/23.39 |
| 6,530,260 B1 * | 3/2003 | Mustacich et al. | 73/23.41 |
| 7,958,774 B2 * | 6/2011 | Brand et al. | 73/61.55 |

* cited by examiner

*Primary Examiner* — Robert Clemente
(74) *Attorney, Agent, or Firm* — Barry L. Davison; David Wright Tremaine LLP (57) ABSTRACT

In a fast gas chromatograph (GC) method and device for obtaining fast gas chromatography analysis, a capillary gas chromatography column is inserted into a resistively heated metal tube located mostly outside a standard gas chromatograph oven, which may serve as a heated transfer line to a flexible column that enters the resistively heated metal tube from its injector and exits into its detector. The fast GC device enables less than one minute full range temperature programming and cooling back analysis cycle time. The fast GC according to one embodiment is combined with mass spectrometry with supersonic molecular beams for the provision of fast analysis cycle time together with highly informative mass spectral information for improved sample analysis and identification.

36 Claims, 4 Drawing Sheets

FAST GAS CHROMATOGRAPH METHOD AND DEVICE FOR ANALYZING A SAMPLE

FIELD OF THE INVENTION

Particular aspects relate to a fast gas chromatograph (GC) method and device for obtaining fast gas chromatography and/or fast gas chromatography mass spectrometry with supersonic molecular beams analysis.

BACKGROUND OF THE INVENTION

Gas chromatography is a central analytical technology having a large variety of applications in a broad range of fields, especially when used in association with mass spectrometry for improved sensitivity, selectivity and sample identification capability.

However, while gas chromatography (GC) is a powerful analytical tool, GC analysis requires long analysis times, typically in the order of 30-60 min. In addition, the range of compounds amenable to conventional gas chromatography analysis with standard gas chromatography columns (typically 30 m) combined with standard column flow rates such as 1 ml/min is limited to stable and volatile compounds only, since thermally labile compounds can degrade due to overheating while low volatility compounds are unable to elute.

In view of the long time associated with standard GC analysis, several fast GC systems have been developed that incorporate low thermal mass devices that provide fast temperature programmable heating and cooling rates for the GC separation columns.

For example, Rounbehler, et al describe in U.S. Pat. No. 5,808,178 a fast GC module named "Flash GC" which is based on a capillary GC column inside a resistively heated metal tube which can be quickly heated and cooled due to its low thermal mass to achieve rapid separation of analytes. Resistive heating is based on the principle that the temperature of a metal increases when an electrical current is passed through it, and the metal resistance increases, consequently, in a manner that can be predicted. The metal temperature can be determined by its electrical resistance measurements and can be adjusted by controlling the amount of power applied to it to reach a defined temperature set point.

However, as is well known, fast GC is the art of compromises, and speeding up the GC temperature programming rate alone can result in the reduction of GC separation efficiency, column lifetime, range of compounds amenable for analysis, sample capacity, linear dynamic range and sensitivity, combined with increased cost of columns which can be coupled with the cost of the whole fast GC module.

Furthermore, fast GC and particularly fast gas chromatography mass spectrometry (GC-MS), in which a mass spectrometer serves as the GC detector, require much more than just fast temperature programming rate of the GC oven. For example, standard splitless sample injection takes a few minutes, since it requires one minute just for sample cryo-focusing at low GC oven temperatures plus additional time for heating to the analytically useful column temperature and cooling back. While split injection may reduce the time required for sample introduction into the column, it leads to unavoidable and often unacceptable loss in limit of detection and sensitivity. Furthermore, fast GC may give rise to narrow GC peaks which may require fast detector response time and in case of mass spectrometry it requires the combination of fast scan speed and fast ion source response time. Above all, there is a major difference between fast GC and fast GC-MS in that in GC-MS the mass spectrometer adds an additional dimension of sample separation and selectivity which can be further enhanced with tandem mass spectrometry (MS-MS) such as in triple quadrupole mass spectrometry systems. The basic idea is that in fast GC-MS GC separation can be traded (and some chromatographic peaks co-elution can be allowed) for having additional separation of the MS while in fast GC, the GC separation is its prime feature which often cannot be reduced.

Thus, despite the obvious merit of having fast GC and/or fast GC-MS and its availability in the market, the vast majority of GC and GC-MS analysis still takes more than 20 minutes.

In the last 18 years, Applicants' research has been focused on the development of a new type of GC-MS which is based on the use of supersonic molecular beams (SMB) (also named Supersonic GC-MS). Supersonic GC-MS is based on a GC and MS interface with SMB and on the electron ionization (EI) of vibrationally cold analytes in the SMB (cold EI) in a fly-through ion source. This ion source is inherently inert and further characterized by ultra fast response time and vacuum background filtration capability. The same ion source also offers a mode of classical EI. Cold EI, as a main mode, provides enhanced molecular ion combined with effective library sample identification which is supplemented and complemented by a powerful isotope abundance analysis method and software. Applicants note that the feature of enhanced molecular ion also implies enhanced separation power of the mass spectrometer since, as is well known, matrix interference is exponentially reduced with mass. In addition, the range of low volatility and thermally labile compounds amenable for analysis is significantly increased with the Supersonic GC-MS due to the use of contact-free fly-through ion source and the ability to lower sample elution temperatures through the use of high GC column carrier gas flow rates. Another important feature of the Supersonic GC-MS is its compatibility with high column flow rates without any adverse effect on its sensitivity due to the availability of a differential vacuum chamber for the supersonic nozzle. As will be shown below, this feature is very important for the combination of the novel fast GC method and device according to the present invention with the Supersonic GC-MS.

BRIEF DESCRIPTION OF THE INVENTION

It is an object of the present invention to provide an improved method and system for fast gas chromatography analysis.

In accordance with one aspect of the invention, there is provided a method for fast gas chromatography analysis, said method comprising:

injecting a sample to be analyzed into a gas chromatograph injector that is coupled to a gas chromatography capillary column;

transferring said sample in said injector into said capillary column with a carrier gas flow;

transferring said capillary column through a gas chromatograph oven as a flexible non-rigid capillary into a resistively heated metal tube having opposing input and output ends;

locating the input and output ends of said resistively heated metal tube near a hole in the gas chromatograph oven body so that a substantial portion of said column in said heated metal tube is located outside said gas chromatograph oven and so that said input and output ends project a short distance inside said gas chromatograph oven;

introducing an end of said portion of said capillary column that is outside the gas chromatograph oven from said heated metal tube into said gas chromatograph oven as a flexible capillary;

connecting said flexible capillary with a transfer line that leads into a gas chromatograph detector;

connecting both ends of said resistively heated metal tube to a power supply; and resistively heating said heated metal tube in a time programmed manner to facilitate fast temperature program of said capillary column;

wherein said capillary column is flexibly connected to said gas chromatograph injector and detector.

In accordance with another aspect of the invention, there is provided a fast gas chromatograph device for enabling fast gas chromatography analysis, the device comprising:

a gas chromatograph injector;

a capillary gas chromatography column;

a connector for connecting said capillary column with said gas chromatograph injector;

a source of carrier gas flow for the transferring of sample vapor in said injector into said capillary column;

a metal tube that is adapted to be resistively heated and that is located mostly outside a gas chromatograph oven and that is coupled via a flexible capillary column to said gas chromatograph injector and detector;

a transfer line with a connector for connecting said flexible capillary column to a gas chromatograph detector;

said input and output ends of said metal tube being located near a hole in the gas chromatograph oven body so that a substantial portion of said column in said metal tube is located outside said gas chromatograph oven;

means for coupling a power supply to both ends of said metal tube for its resistive heating; and a controller configured for resistively heating said metal tube in a time programmed manner to facilitate fast temperature program of said capillary column in said heated metal tube.

BRIEF DESCRIPTION OF THE DRAWINGS

The invention will now be described in connection with certain preferred embodiments with reference to the following illustrative figures, so that it may be more fully understood. With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. It will be apparent to one skilled in the art that there are several embodiments of the invention that differ in details of construction, without affecting the essential nature thereof, and therefore the invention is not limited by that which is illustrated in the figures and described in the specification, but only as indicated in the accompanying claims, with the proper scope determined only by the broadest interpretation of said claims.

In the drawings.

DETAILED DESCRIPTION OF THE INVENTION

Figure 1:
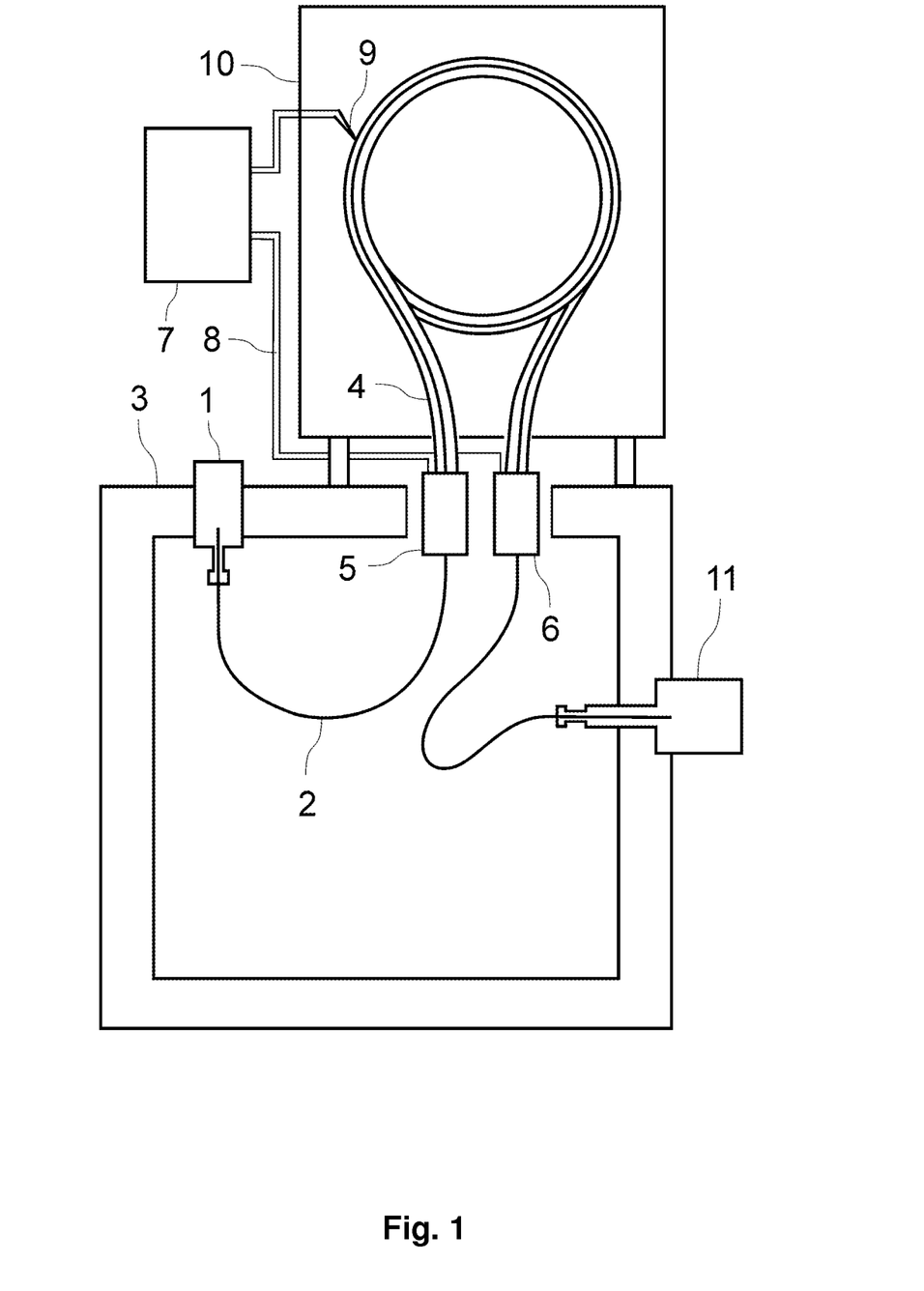
FIG. 1 is a schematic diagram illustrating the fast gas chromatograph device, according to the present invention.

FIG. 1 shows schematically the novel fast gas chromatograph according to the present invention. A sample is injected as usual manually or preferably with an auto sampler into a GC injector (1) which is connected to a standard capillary column (2). Unique to our method and device is the fact that the capillary column is connected in a flexible non-rigid way as is normally done with standard GCs but in contrast to most fast GCs. The capillary column itself is typically made from highly flexible Vespel coated fused silica tubing, coated on its inside with a thin sorption film. Thus, the column is immersed in a standard GC oven (3) which as a result must be heated to a temperature that corresponds to the temperatures of the injector and detector to eliminate cold spots (in contrast to hitherto-proposed fast GC methods and devices). The capillary column is introduced into a metal tube (4) that can be resistively heated and that possesses an inlet (5) and an outlet (6), both of which are connected to a current programmed power supply (7) via electrical connections (8). The power supply (7) includes temperature sensor feedback and is capable of being current programmed to provide a temperature program (with time). The temperature can be measured with a thermocouple (9), or via the resistance of the metal tube which increases with its temperature in known manner. Otherwise, the current value can be used alone to represent the temperature via temperature calibration tables. The capillary column in its resistively heated metal tube is mostly located in an air-cooled enclosure (10) which is typically placed above the standard GC oven. The inlet (5) and the outlet (6) of the heated metal tube are located just at the edge of the standard GC oven housing so that the portion of it that is not resistively heated is located inside the GC oven (so that it will be heated to the standard GC oven temperature). The portion that is resistively heated is located just outside the GC oven to avoid or significantly reduce its double heating by both the GC oven and resistively heated tube, which can lead into an over heated column section (hot spot) as well as to avoid unheated sections of the GC column (cold spot) between the resistively heated tube and GC oven. Both hot spot and cold spot, permanent or temporary (during temperature program) appearance are unacceptable. Hot spot causes the reduction of the column lifetime, induces local damage to the column separation film and protective Vespel external film, increases column bleed and degrades thermally labile analytes, while cold spot affects chromatographic peak shape and induces peak tailing and delays or precludes the elution of low volatility analytes. Therefore, the proper location of the inlet (5) and outlet (6) unions and their design is aimed at minimizing both hot and cold spots. The capillary column output is flexibly connected to the separately heated detector transfer line (11). According to the invention, the detector can be any standard GC detector such as a flame ionization detector (FID) but it is preferably a mass spectrometer (MS) with a Supersonic Molecular Beam (SMB).

While the essence of the fast GC invention is shown in FIG. 1 and described above, additional details as below can further help in improving the description and in the illumination of a few additional aspects of the fast GC according to the present invention.

One of the important features of the fast GC according to the present invention, which differentiates it from all other types of fast GCs is that the capillary column is not rigidly connected to the metal tube and can freely slide (inserted) into it. Therefore, the column can be pushed into the heated metal tube or pulled out and as a result column replacement can be performed by the user at relatively little cost. In order to facilitate such easy column insertion, the fast GC heating metal tube is located in its house as a relatively large circular structure (i.e. with 12 cm diameter) with smooth curves while entering into the standard GC oven. In addition, both the inlet and outlet ends of the metal tube heaters are machined with chamfer surfaces, typically having an angle of 60° to ease the column insertion without a danger of breaking it. Furthermore the column is inserted in such a way that both ends of the capillary column protrude out of the heated metal tube to have easy connection with both the injector and detector transfer line. Thus, column replacement can be performed with a small portion of a standard capillary column (such as 30 m long) that is cut to a length a little longer than the length of the heating metal tube such as about 2.5 m for 1.5 m heating metal tube length and as a result the heating metal tube and its holding structure are not replaced while the capillary column is replaced or even not disassembled. Note that as a result the capillary column is not bundled with its metal tube heater and its mounting holder. Consequently, the user can select and install in the fast GC according to the present invention any GC column from a huge set of commercially available columns (column internal diameter, film type, film thickness) from several manufacturers. The column extension before and after the heating metal tube further enables flexible choice in column length, which enables its periodic trimming if its input end is contaminated by low volatility sample matrix, and provides easy handling when inserting the capillary column into both the GC injector and detector transfer line.

Since unique to this method of fast GC is the fact that the standard GC oven serves as a part of the transfer line from the injector and to the detector during the fast GC operation, it must be heated to a temperature around that of the detector transfer line such as in the range of 250-350° C. Since such high temperature can lead to column bleed, the analytical column of the fast GC can also be connected to the injector and detector via unions and deactivated fused silica capillary transfer lines.

The fast GC method according to the present invention is characterized by several additional unique operational parameters. For example, the carrier gas flow rate is typically higher then 4 ml/min and can be in the range of 20-40 ml/min. This approach represents a reduction in the fast GC separation power for achieving faster analysis, greater sample capacity and linear dynamic range (LDR), and column robustness and extended range of compounds amenable for analysis. The reduced fast GC separation is compensated for by increased separation power of the detector, particularly when a mass spectrometer with supersonic molecular beams serves as the detector. Similarly, the fast GC column according to the present invention is short, usually with column length below 4 m and typically with only 1.5 m column length. Column length reduction is required to enable the desirable high column flow rate and facilitate ultra fast GC separation. In addition, it enables easier column replacement into the heating metal tube which is practically impossible with standard 30 m long columns. Consequently, the combination of short column, high column flow rate and low thermal mass of the resistively heated metal tube enables a full analysis cycle time of less than one minute.

While most fast GC modules that aim at the conversion of standard GC into fast GC are located inside the standard GC oven, an available design is based on the conversion of the standard GC front oven door into the fast GC module holder. A preferred arrangement of the fast GC according to the present invention is based on the mounting of the fast GC module on top of the oven of the standard GC. Consequently, the fast GC is typically interfaced with the standard GC through available holes for a second injector or detector. An important advantage in such mounting is that the standard GC oven door can be fully and freely open as usual for service including for column assembly and its connection and insertion into the injector and detector. This arrangement also implies that the fast GC module is relatively small and that its control electronics can be separated from it and conveniently located at a side of the GC. While the fast GC module is relatively small, it is designed to be big enough to accommodate the resistively heated metal tube in a circular diameter of about 10-15 cm while being mounted on a holder via the support of very low thermal mass object such as thin Kapton foils that are also good thermal insulators to minimize the cooling of the metal tube that might touch it. The fast GC module typically further include an air cooling fan which can be time programmed to facilitate faster cooling down of the metal tube heater when needed.

An important yet delicate portion of the fast GC according to the present invention is its portion where the resistively heated metal tube is interfaced with the standard gas chromatograph oven. This interface must be designed in a way to minimize both temporary thermal cold spots and hot spots. Thus, Applicants found that a preferred design includes the location of the capillary column insertion input and output ends at about 1 cm inside the standard GC oven so that they are heated by the GC oven to its temperature. This interface also includes the input and output ends of the resistively heated metal tube and its electrical contacts. The interface is designed to be short yet thermally conductive and with high temperature gradient on the resistively heated metal tube above it to minimize the magnitude and length of any doubly heated hot spot. This hot spot if diagnosed can be further reduced by the extension of the electrical contacts, which are also heat conductors, one or several cm above the interface.

While the fast GC according to the present invention can be designed as an independent fast GC system it also preferentially targets the conversion of a standard GC with its injector and detector into a fast GC. Thus, such a conversion is preferably performed without the removal of any substantial component from the standard GC, including the GC autosampler, injector, detector, pneumatic system and gas flow controls and data analysis and software. As a result, a standard GC can be converted into a fast GC by a simple add-on low cost fast GC device according to the present invention.

Summary of Unique Features of the Fast GC According to the Present Invention

The following are major aspects and advantageous features of the novel fast GC method and device, which differentiate it from known fast GC:

1. Flexible connections with the GC injector and detector inside a hot standard GC oven. GC is much more than just the GC oven and as a system it includes an auto sampler, injector and its gas supply system, separation column and its flow rate control, GC oven and its temperature control, detector and means for data analysis and reporting. Thus, it is highly desirable to convert a standard GC into a fast GC via the replacement of only its oven with a fast GC oven module. However, the combination of a fast GC with the standard GC injector and detector gives rise to problems of cold spots between the fast GC module and the GC injector and detector. Consequently, most fast GCs use a heat conductive rigid structure between the fast GC module and the GC injector and/or detector, and this structure serves to conduct heat from the heated injector and detector to reduce the temperature gradient between the fast GC module and injector and detector. For example, Rounbehler, et al. in their U.S. Pat. No. 5,808,178 describe a fast GC method wherein cross sections of the connectors are substantially larger than cross sections of the sheath so that the connectors provide rigid structures for mechanically connecting the flash chromatography module to a gas chromatography system. The method and device according to the invention do not employ a rigid structure for mechanically connecting our module to a GC system. In contrast, we use a highly flexible and non rigid capillary column for such connection and our fast GC input and output are not connected to a GC system with mechanically rigid devices. This represents a major deviation from the above art and leads to several important advantages as detailed below. Since our connections are flexible, we must uniquely operate our fast GC with a hot oven of the standard GC to prevent cold spots between the fast GC module and the standard GC injector and detector. Since the standard GC oven is hot, we also must remove the fast GC heated zone outside the standard GC oven and place the majority of the fast GC separation column strictly outside the standard GC oven. Furthermore, the electrical contacts of our fast GC are preferably placed in the vicinity of the exit of the standard GC where the two heated sections are thermally separated to minimize and/or eliminate hot spots due to possible double column heating by both the fast GC and standard GC ovens, as well as possible cold spots if the separation of heated zones is too large. These unique few changes surprisingly provide several very important benefits as below.

2. Elimination of cold spots and having extended range of compounds amenable for analysis. Applicants' methods are different from other low thermal mass (LTM) fast GC in having the standard GC oven heated in accordance with and in relationship to the injector and detector transfer line temperatures to prevent cold spots at the flexible sections of the separation capillary column. Thus, Applicants' methods and devices are uniquely characterized in having the standard GC oven actively participating in the elimination of cold spots between the fast GC and injector and/or detector. Consequently, the standard GC oven temperature according to the present invention is user defined and not at room temperature. According to other L™ fast GC methods, cold spots particularly at the detector transfer line are inevitable since the standard GC detector (and injector) are designed to have temperature gradients between the GC oven that can be at low temperatures and the hot injector and detector and the edge of their transfer lines are not adequately heated and as a result form a cool section (cold spot). This cold spot induces a pronounced chromatographic peak tailing, or otherwise requires much higher injector and or detector temperatures. As a result of the inevitable cold spot, large molecules with low volatility are incompatible with most fast GCs, which are limited to relatively volatile organic compounds. Our fast GC is uniquely characterized by having increased range of compounds amenable for analysis due to the elimination of cold spots, the use of short columns with high column flow rate and the use of Supersonic GC-MS and its fly through ion source.

3. Flexible column length. The length of the column according to Applicants' methods and devices is flexible since the column can arbitrarily extend beyond the heated metal tube of the fast GC module at any desirable length. As a result, the user does not need to have a precise precut column and can have great flexibility and ease in column assembly and replacement without a danger of column breakage. Furthermore, the column can be connected using union connectors and a deactivated fused silica capillary transfer line into both the injector and detector. The column connection with the injector with such transfer line (also known as retention gap) is known to further improve the analytical column lifetime.

4. Increased fast GC column lifetime. The analytical column lifetime is significantly extended with fast GC according to the present invention for a few reasons. Since according to our method short wide bore columns with 0.32 mm internal diameter (ID) (or 0.25 mm ID) are preferably used they are much more robust than thinner columns with lower ID. In addition, the use of such a column in combination with high column flow rate increases the column sample capacity, system linear dynamic range and column robustness and lifetime. Furthermore, since the present column freely extends beyond the heating metal tube it can be cut as needed to remove its upstream portion near the injector which is periodically contaminated by low volatility matrix compounds and dirt. This practice is normally used with standard GC but is practically impossible with fast GCs which are rigidly connected to the injector and detector hence do not allow the user to cut the column.

5. Lower cost of use. The price of columns according to Applicants' exemplary methods and devices is far lower than with known fast GC methods since the present replacement column is just a piece of any standard capillary GC column of choice, the column lifetime is much longer as explained above, and a new short capillary column can be inserted many times into the fast GC oven tube for new use. Thus, with Applicants' fast GC the user may replace only the capillary column without its heating tube, which is in contrast to other fast GC methods. Currently, fast GC short columns are sold for about $2000 while standard GC columns are sold for $500. A new column that is used with our fast GC is typically a 1.5-2.5 meter capillary that is cut from a standard 30 m column; hence its cost is only about $25-40. Applicants note that in other fast GC devices the column is either permanently combined with its heating oven or requires a special coating for microwave heating or resistive heating which restricts its available selection and markedly increases its price.

6. Flexible fast GC module which is compatible with any standard GC model. According to the present exemplary methods and devices, the fast GC module is external to the GC oven and only a non rigid flexible capillary column extends beyond its low thermal mass heating tube. As a result, the capillary column can be connected in its standard way with any GC connector style of the injector and detector, including mass spectrometer detector. Unlike with the rigid connector design of some fast GC which must be compatible with a specific GC model and injector/detector, according to the present invention the standard GC injector and transfer line are communicated with the capillary column in the same way as they were designed to. Consequently, a one model of our fast GC can be coupled with any standard GC system of any vendor.

7. Fastest Fast GC module. The exemplary fast GC method and device according to the present invention is characterized by the smallest amount of thermal mass, hence, in combination with short columns and high column flow rates it enables the fastest heating and cooling back rates and thus enables sub one-minute full analysis cycles time for broad range of applications. Applicants' fast GC is unique in having a thin metal tube as its heater without any insulation from ambient air, thereby enabling maximum heat exchange rate and as a result a very fast cooling rate.

8. Supersonic GC-MS advantages. The present exemplary fast GC is uniquely compatible and combined with the Supersonic GC-MS. As a result, it forms the best fast GC-MS in terms of speed of analysis, sensitivity, range of compounds amenable for analysis and improved sample identification capability.

9. Combined fast GC and standard GC in a single system. Applicants' exemplary methods and devices are further characterized by improved operational flexibility in having the ability to connect two (or three) columns to the same detector via a standard T union since our column end is a standard capillary column. Thus, one can use the fast GC module in combination with a standard GC column that is connected from a second standard GC injector. As a result, the present fast GC can uniquely serve for screening, while in the case of detection of a suspected compound, the method can be changed by a click of the mouse and the screening can be followed by a confirmation run with increased separation power of a standard GC column. The feature of flexible dual use of fast GC and standard GC in a single GC system is of considerable practical importance as further described below.

Figure 2:
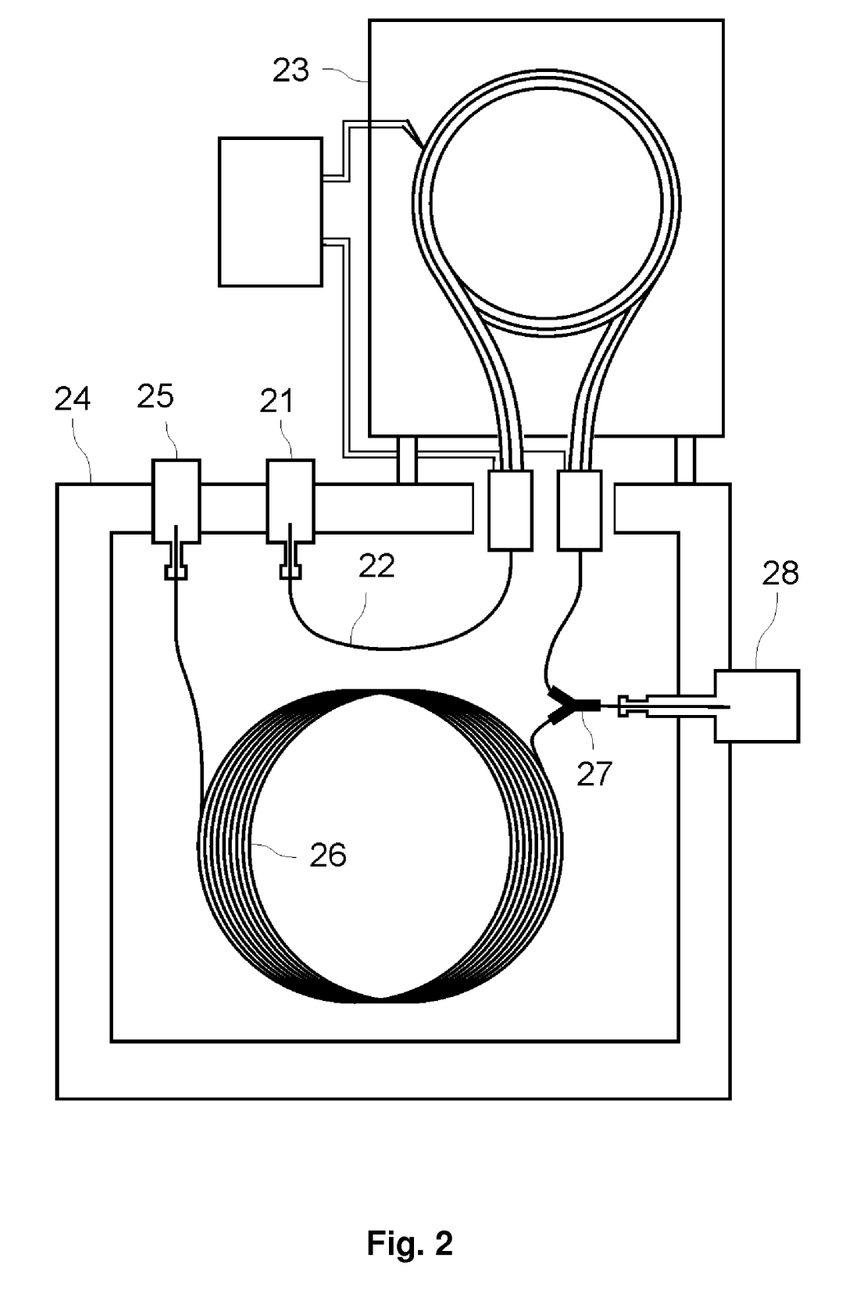
FIG. 2 is a schematic diagram illustrating an additional embodiment of the fast gas chromatograph device of FIG. 1, which combines the fast gas chromatograph and a standard gas chromatograph in a one system having two injectors and columns that are connected to a one detector.

Since fast GC and/or fast GC-MS according to the present invention involves up to an order of magnitude loss of GC separation resolution and peak capacity, it is often desirable to combine the fast GC and standard GC with MS detector in the same system. The use of a flexible capillary column which extends outside the resistively heated metal tube of the fast GC module enables an easy way for combining two column outputs simultaneously into the mass spectrometer transfer line via a standard T union. As a result, easy and automated switching from fast GC-MS screening to standard GC-MS confirmation is enabled. FIG. 2 shows the combination of fast GC-MS according to the present invention and standard GC-MS in a single system. The sample can be injected for its fast GC screening via injector (21) into fast GC short column (22) that enters into the fast GC low thermal mass heating unit (23). The standard GC oven (24) further includes a second GC injector (25) that serves to inject samples into a standard capillary column (26). Both the fast GC short column (22) and standard column (26) are connected to a low dead volume Y connector (27) which is further connected via a transfer line (28) into the mass spectrometer GC detector. The mass spectrometer detector is preferably operated with a supersonic molecular beam interface and its fly-through EI ion source which can easily handle the flow rate of two columns simultaneously without adversely affect the sensitivity (including the high column flow rate of the fast GC column).

Figure 3:
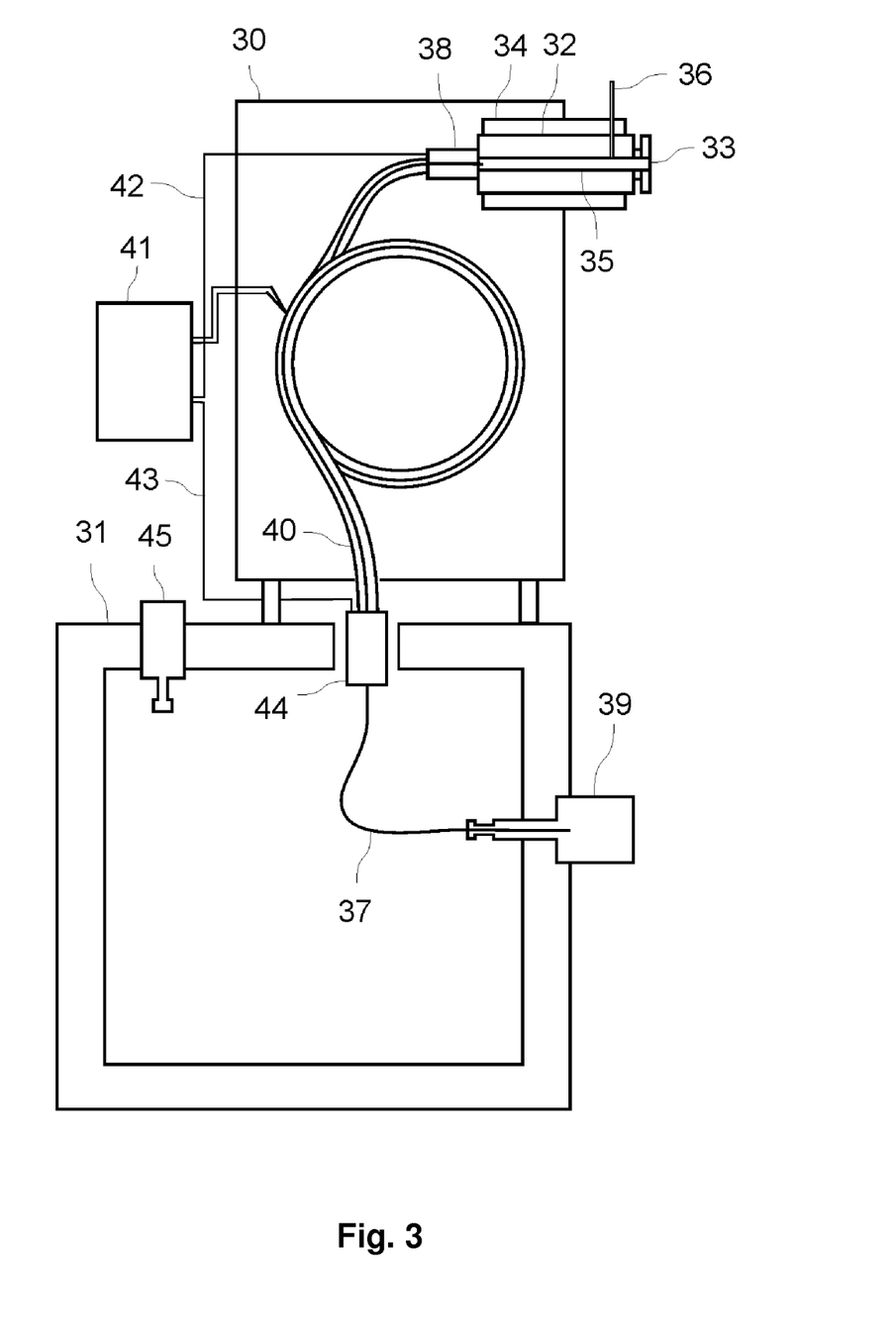
FIG. 3 is a schematic diagram illustrating an additional embodiment of the fast gas chromatograph device of FIG. 1, which enables sample injection into an open probe injector at ambient atmosphere.

FIG. 3 shows the combination of fast GC according to the present invention with an Open Probe. The open probe consists of a probe oven that is mounted onto a MS transfer line such as of a Supersonic GC-MS, which is open to room air while having a helium purge out flow protection to eliminate or reduce air leakage into the open probe oven and MS ion source to a negligible rate. As shown in FIG. 3, the Open Probe fast GC module (30) is mounted on a standard GC oven (31). The sample is introduced into the open probe sub system (32) via its opening (33). The open probe is heated by a heater (34) and contains an internal inert liner (35) in addition to an inert gas inlet (36). A fast GC short column (37) is connected into the open probe at its input side (38) and flexibly connected to the mass spectrometer transfer line (39) at its output side. The fast GC further contain low thermal mass tube heater (40) that is resistively heated by power supply (41) through electrical contacts (42) and (43). The fast GC communicates with the standard GC through its interface element (44). The standard GC may further contain a second injector (45) and column as described above.

The Open Probe is characterized by having the fastest (by far) analysis cycle time among all MS probes, which can be less then 10 seconds, and it is a very flexible and easy to use MS probe. Open Probe MS can clearly benefit from the addition of ultra fast GC separation and as a result can provide sub one-minute ultra fast GC-MS analysis from the sample to the results. Thus, the combination of the open probe with fast GC-MS means that fast analysis also includes fast sample preparation for injection. Otherwise, there is scarcely much reason to use fast GC-MS of one minute if sample preparation takes for example one hour. Applicants view the combination of the open probe with the fast GC according to the present invention and Supersonic GC-MS as the ideal system for achieving the fastest analyses. Applicants note that a fast GC which is used in combination with the Open Probe is slightly different then fast GC which is used with standard GC injector. The main difference is that, as its name implies, the Open Probe operates at ambient pressure and hence must deliver a sample to a sub ambient GC detector such as a mass spectrometer. The inability to use high injector pressure can limit the fast GC column length and flow rate. Furthermore, the fast GC is typically connected to the Open Probe in a rigid way while the fast GC is flexibly connected only to the MS transfer line via the standard GC oven.

Another important area of use of fast GC according to the present invention is in comprehensive two dimensional LC×GC where the LC separated or coeluted compounds are periodically injected into a GC for further orthogonal GC separation based on the order of sample compounds boiling points. Since LC×GC involves 50-100 GC analyses for each LC run, the reduction of the GC analysis time is crucial for having a practical LC×GC analysis which otherwise can take over two days, and short GC cycle times of under one minute (or as short as possible) are desirable and can reduce the LC×GC analysis time to 1 hour instead of two days. Thus, the fast GC according to the present invention seems ideal for LC×GC and particularly for LC×GC-MS with SMB.

Similarly, the fast GC according to the present invention can serve as the second GC column in comprehensive two dimensional GC×GC and particularly in two dimensional GC-GC and/or GC-GC-MS in which a heart cut from the sample compounds that elute in a first column is further separated by a fast GC with a column that has different polarity in comparison with that of the first column. Both modes of two dimensional GC×GC and GC-GC can be performed with a pulsed flow modulation according to U.S. Pat. No. 7,518,103 of A. Amirav. Such pulsed flow modulation is suitable for the combination of the fast GC second column with supersonic molecular beam and is compatible with its high second column flow rate requirements.

Example 1

Figure 4:
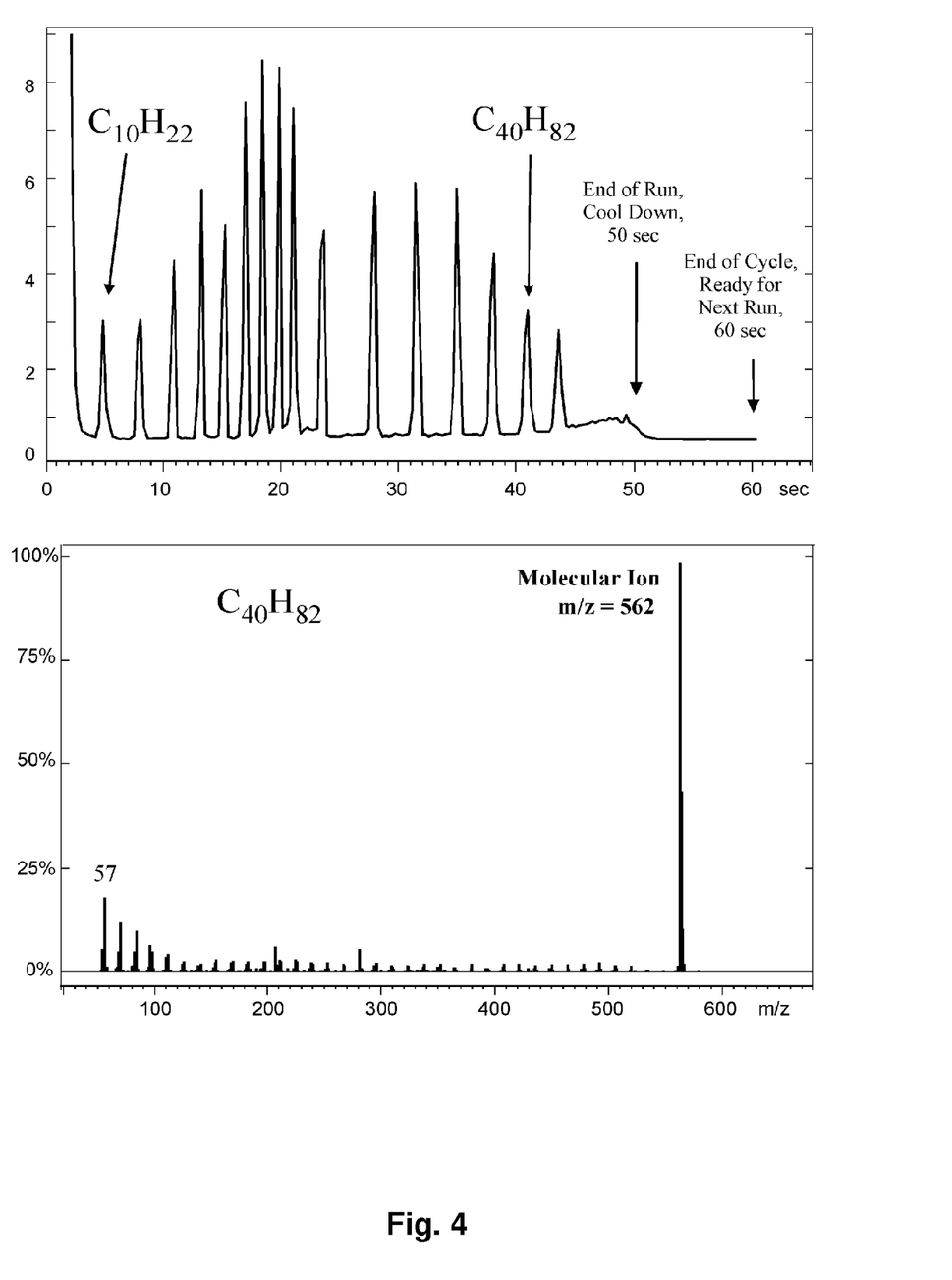
FIG. 4 illustrates typical experimental results obtained with the fast gas chromatograph device of FIG. 1 coupled with a mass spectrometer with supersonic molecular beams in the analysis of a mixture of hydrocarbons ranging from $C_{10}H_{22}$ up to $C_{44}H_{90}$.

A Broad Volatility Range of Linear Chain Hydrocarbons was Analyzed Using the Inventive Fast GC in Combination with a Mass Spectrometer with Supersonic Molecular Beams Reference is now made to FIG. 4, in which typical results of an experiment using the present invention are presented. In FIG. 4 the operation of the fast GC according to the present invention in combination with a mass spectrometer with Supersonic molecular beams is demonstrated in the analysis of a broad volatility range of linear chain hydrocarbons. The fast GC was mounted on a Varian model 3800 gas chromatograph (Varian, Walnut Creek Calif.) that is coupled with a triple quadrupole based mass spectrometer with supersonic molecular beams. The experimental system is described in detail in a paper by A. B. Fialkov, U. Steiner, L. Jones and Aviv Amirav, Int. J. Mass. Spectrom. 251, 47-58 (2006). The hydrocarbons commercial mixture included 17 compounds in the range from $C10H22$ up to $C44H90$, each at 100 ng/μL concentration in hexane. It was injected into a Varian model 1177 injector with a split ratio of 4:1 so that 20 ng of each sample compound was injected into the column. The column was a 2.5 m long 0.25 mm ID fused silica capillary column with 0.25μ. DBSMS UI film (Agilent Technologies, Folsom Calif.) that was inserted into 1.7 m metal tube with 0.53 mm ID and 0.75 mm OD (Restek, Bellefonte Pa.). The metal tube was coiled three times in 12-13 cm diameter loops and contacted only Kapton foil (0.125 mm thick) on its way from the top of the Varian 3800 GC into its oven where inlet and outlet connector unions penetrated 1 cm inside the oven. Helium served as the carrier gas at a flow rate of 20 ml/min. Homemade fast GC software controlled the fast GC heating rate via a current programmable power supply that was programmed in the 0-3.4 A range. A cooling fan was also used to speed up the fast GC cooling and its operation was time-programmed by the control software. As demonstrated in FIG. 4, all the 17 hydrocarbons were fully separated in 45 seconds despite the huge difference in their boiling points which was 142° C. for $C10H22$ and 693° C. for $C44H90$. In addition, only 10 s were required for cooling back the column so as to be ready for the next analysis cycle, thus providing ultra fast GC-MS analysis time. An additional very important feature of the system which is demonstrated in FIG. 4 is the observation of molecular ion even for $C40H82$ which is unique for the Supersonic GC-MS and which demonstrates the increased selectivity and information content provided by GC-MS with SMB.

Discussion of the Area of Fast GC in Relation to the Novel Fast GC Method and Device According to the Present Invention Fast GC represents an art of trade-offs in which speed is gained at a cost of reduced performance in other GC operational parameters. Thus, a good fast GC approach must be based on a smart choice of those operational parameters that are traded for achieving faster analysis.

Standard GC is typically operated with 30 m long capillary columns with 0.25 mm ID and 1 ml/min column flow rate. According to the theory of GC, the maximum allowed temperature programming rate in which the column separation is retained is 10° C. per void time. Void time is the time that is required for the carrier gas to flow through the column from injector to detector, and for a standard column and flow rate as above it is ~90 seconds. As a result, the maximum temperature programming rate which is used in combination with full standard GC separation power is 7° C./min. With such temperature programming rate, full temperature range analysis from 50° C. to 350° C. sums up from: 1 minute for splitless injection at 50° C., 43 minutes temperature programming to 350° C., 2 minutes at 350° C. and about 4 minutes cooling back and equilibration time with total analysis cycle time of 50 minutes. Obviously, most analysis can employ 10° C./min with only negligible/minor loss in separation resolution and with a typical range of temperature program of only 250° C. such analysis can take only 30 minutes. If reduced GC separation can be tolerated, 5 meter columns can be used with 60° C./min temperature programming rate and the total analysis time can be reduced even to 10 minutes with standard GC but with a loss of more than a factor of 6 in the number of separation plates and about a factor of 2.5 in peak capacity. The standard column with 0.25 mm can be replaced with a short microbore column which can provide such fast 10 minutes analysis with smaller loss in the GC separation capability but with a major loss in sample capacity, column robustness, linear dynamic range and column lifetime. In fact, the use of such microbore columns defies the purpose of fast GC since the combination of reduced column life time with reduced analysis time implies that the column replacement frequency will be significantly increased with its associated cost and downtime.

It is important to note that while standard GC is typically operated with a temperature programming rate in the range of 5-10° C./min the standard GC oven is capable of temperature programming rate of up to 120° C. at low temperatures and 50-60° C. around 300° C. However, if 60° C./min is used with standard columns the analysis will be hampered by a loss of about a factor of 8 in the number of separation plates since most of the time the sample compounds will not be retained in the too hot column and only the initial portion of the column will be used for effective separation. Furthermore, the elution temperatures will be increased by over 60° C. (20° C. per each factor of two increased temperature programming rate above 7° C./min) and as a result thermally labile compounds will degrade, low volatility compounds will elute at the high temperature plateau end of the run (or will not elute) with increased column bleed and ghost peaks chemical noise, and thus, the range of compounds amenable for analysis will be sacrificed and reduced.

According to a preferred method of operation of our fast GC we use 1.5 meter 0.32 mm ID capillary column with 20-30 ml/min column flow rate. Even bigger capillary columns with 0.53 mm ID can be used with the advantage of having much lower flow impedance. Due to the combination of column length reduction by a factor of 20 and column carrier gas flow rate increase by a factor of 20 the number of separation plates is significantly reduced by about a factor of 400 which results in a loss of GC separation resolution and peak capacity by a factor of 20. Such loss cannot be tolerated by most standard GC analysis requirements. However, as explained below, when fast GC-MS analysis is considered, particularly with the Supersonic GC-MS and/or GC-MS-MS, the merits of Applicants' methods and devices far outweigh any limitation in reduced GC separation capability.

The use of 1.5 meter column with 20-30 ml/min column flow rate results in the reduction of the void time by a huge factor of 400. Consequently a temperature programming rate of 45° C./second (2700° C./min) can be used and full range temperature programming can take only 6-7 seconds. However, since even with the low thermal mass fast GC heating tube, cooling down may take 10 seconds, only limited gain in time is achieved by using such fast temperature programming rate. A better method of fast GC operation is based on using a temperature programming rate of 10° C./second which results in 40° C. lower elution temperatures to significantly increase the range of compounds amenable for analysis. Consequently, full analysis cycle takes a few seconds for sample cryo-focusing, 40 seconds temperature programming, 10 seconds cooling back time and less than 5 seconds equilibration time for the total of less than one minute per analysis, which is an order of magnitude faster than can be achieved with standard GC. It is important to realize that the use of high column flow rate is essential for having a useful fast GC since flow rate reduces the void time, thereby enabling fast temperature programming rate combined with increased range of compounds amenable for analysis as opposed to reduced such range as encountered with other fast GC methods and devices. An additional very important attribute of the use of high column flow rate is that standard sample injections are correspondingly faster, and with 30 ml/min standard splitless injection may take only two seconds instead of the usual one minute. Without such injection time reduction, splitless (or split with low split ratio) injection may either prohibit fast GC cycle time of less than one minute or correspondingly reduce the sensitivity (with high split ratio split injections) which is unacceptable for many types of trace level analyses. Finally, Applicants note that the ability to use very high column flow rates enables the use of effective flow programming with large high to low flow rates ratios, which provides a faster alternative to temperature programming rate and eliminates the time needed for cooling back. Thus, flow programming can provide an ultra fast alternative to fast temperature programming when only a limited temperature range of up to 100° C. is needed.

Summary of Advantages of Fast GC Method and Device According to the Present Invention in Comparison with Other Fast GC Methods and Devices The novel Fast GC method and device according to the present invention is characterized by the following major advantages in comparison with currently published and available fast GCs.

A) Ultra Fast GC and GC-MS: Applicants' fast GC approach provides a complete solution for all the requirements of fast analysis including fast high flow rate splitless injections, fast temperature programming rate and cooling back with our low thermal mass resistively heated metal tube, tailing-free ultra fast ion source response time and increased MS separation power through the provision of enhanced molecular ions with the Supersonic GC-MS. Thus, according to the present exemplary method and device sub one minute total analysis cycle time can be routinely obtained with the combination of the Supersonic GC-MS and the instant Fast GC, and, when only a limited GC column temperature range is needed, analysis cycle time of only a few seconds can be obtained. Applicants note that the Supersonic GC-MS uniquely further enables the use of additional methods for the reduction of analysis time such as the use of flow programming and backflush.

B) High sample capacity and linear dynamic range: The combined use of wide bore 0.32 mm ID column with high flow rate increases the sample capacity by over two orders of magnitude in comparison with the use of microbore columns with 0.1 mm ID and 1 ml/min or less column flow rate. Sample capacity depends on the volume of the adsorption film of a separation plate hence it usually increases with the third power of the column diameter and linearly with the column flow rate. In addition, the linear dynamic range (LDR) similarly increases with the sample capacity. This improved LDR and sample capacity are important advantages of the present exemplary method and device which makes it very effective for broad range of practical applications.

C) Higher sensitivity fast GC and GC-MS. The ability to use fast splitless injection in combination with the Supersonic GC-MS provides significantly enhanced sensitivity fast GC-MS, in contrast to other fast GC and GC-MS methods that require the use of high split ratio injection in order to have short analysis times.

D) Longer fast GC column lifetime: The increased sample capacity and separation plate height due to the use of high column flow rate and wide bore columns increases the column life time and available number of analyses per column by over two orders of magnitude in comparison with microbore based fast GC. Such large improvement implies that the present exemplary fast GC can be used for analytical areas and applications that other fast GC systems cannot be practically applied to, such as pesticide analysis in complex agricultural matrices or for fast screening of drugs in dirty/complex urine extracts. Applicants analyzed, using the present fast GC in combination with a mass spectrometer with supersonic molecular beams, a range of pesticides in various matrices including incurred Iprodion (0.23 μg/g) and Cypermethrin (0.22 μg/g) in grapes in one minute full scan cycle time followed by one minute MS-MS for confirmation and similarly for Phosmet (1.3 μg/g) and Azoxystrobin (0.3 μg/g) in Apricot. In addition to much greater tolerance to sample matrix contamination, a portion of the short column according to Applicants' method and device can be cut at its inlet end where most of the contamination occur and be used again.

E) Lower cost of columns and use: The fact that the column is short means that it can be easily inserted into its resistively heated metal tube and the fact that the column ends are extended from the fast GC heated tube and are not mechanically connected to it makes it possible to replace only the capillary column without the need to also replace the heating tube oven. As a result, column replacement can cost 50 times less then other fast GC columns. The fact that a new column can cost as little as $25 and it can be available from broad range of capillary column vendors means that the fast GC user can test several column types to properly optimize the column to his specific application need. This is in contrast to some fast GC methods and device that use columns that are available only from a one vendor and that cost over $2000 each since they are sold in combination with their heating oven and rigid connectors.

F) Extended range of compounds amenable for analysis. This important yet surprising feature is unique to the present methods and devices. For example, Applicants analyzed a mixture of hexadecane, anthracene, methylstearate, cholesterol and a heavy compound with molecular weight of 774 ($C_{54}H_{78}O_3$) in less then 20 seconds while the last compound and even cholesterol are not amenable for other types of fast GC.

G) Fast GC-MS with Supersonic Molecular Beams: The fast GC according to the present invention is uniquely compatible with the Supersonic GC-MS which is the only GC-MS technology that can accept the required fast GC high column flow rate of 20-40 ml/min without split. Furthermore, the Supersonic GC-MS accepts such flow rate without any adverse effect on its sensitivity. In addition, the Supersonic GC-MS can uniquely operate with its ion source filament turned on during solvent elution time in splitless injections. One of the reasons for this unique capability is that during solvent elution the supersonic molecular beam is altered, the jet separation stops and only 1% of the solvent enters the ion source. The ability to operate very near the solvent elution time is crucial for effective fast GC-MS operation. The most important feature of the supersonic GC-MS is its increased selectivity via the provision of enhanced molecular ions. Since Applicants' Fast GC method is based on the trade-off of GC separation capability for the many benefits above, its combination with the Supersonic GC-MS provides improved mass spectrometry separation capability via the feature of enhanced molecular ion to offset the lost GC separation. As explained above, the degree of matrix interferences is exponentially reduced by over a factor of 20 each 100 atomic mass unit (amu) higher mass. In addition, MS-MS can be used to further improve the separation power and selectivity of mass spectrometry. Thus, the combination of fast GC according to the present method and device and Supersonic GC-MS uniquely provides a powerful system that combines fast analysis with improved sensitivity, range of compounds amenable for analysis and confidence level in sample identification.

H) Open Probe Fast GC and Comprehensive LC×GC and GC-GC with fast GC. The fast GC according to the present invention is uniquely compatible with other non-standard yet important types of fast GC applications such as fast GC of comprehensive LC×GC, GC-GC and Open Probe fast GC-MS. The Open Probe enables the fastest, easiest to operate and most flexible sampling device and it reduces the time needed for sample preparation, to complement and supplement true fast analysis cycle time to include fast sample preparation. The combination of Open Probe and Fast GC-MS with SMB can provide a very powerful fast analysis from sample preparation to data analysis. LC×GC-MS with SMB can provide improved LC separation combined with extended SMB-MS information and it can clearly benefit from having a fast GC with high flow rate according to our method and device. Heart cut GC-GC can clearly benefit from having fast second column GC analysis to facilitate many heart cuts analyses in a single analysis.

The combination of these eight advantages is surprising, and the exemplary fast GC as disclosed herein provides a powerful new method and device for obtaining fast GC sample separation for its analysis with both standard GC detectors, mass spectrometer detector and particularly with a mass spectrometer with supersonic molecular beams as the fast GC detector.

The invention claimed is:

1. A method for fast gas chromatography analysis, said method comprising:
   injecting a sample to be analyzed into a gas chromatograph injector that is coupled to a gas chromatography capillary column;
   transferring said sample in said injector into said capillary column with a carrier gas flow;
   transferring said capillary column through a gas chromatograph oven as a flexible non-rigid capillary into a resistively heated metal tube having opposing input and output ends;
   locating the input and output ends of said resistively heated metal tube near a hole in the gas chromatograph oven body so that a substantial portion of said column in said heated metal tube is located outside said gas chromatograph oven and so that said input and output ends project a short distance inside said gas chromatograph oven;
   introducing an end of said portion of said capillary column that is outside the gas chromatograph oven from said heated metal tube into said gas chromatograph oven as a flexible capillary, wherein the capillary column and the resistively heated metal tube are configured such that transferring the capillary column through the gas chromatograph oven into the resistively heated metal tube and introducing the capillary column from the heated metal tube into the gas chromatograph oven is reversible, without removal of the resistively heated metal tube;
   connecting said flexible capillary with a transfer line that leads into a gas chromatograph detector;
   connecting both ends of said resistively heated metal tube to a power supply; and
   resistively heating said heated metal tube in a time programmed manner to facilitate fast temperature program of said capillary column;
   wherein said capillary column is flexibly connected to said gas chromatograph injector and detector.

2. The method according to claim 1, wherein:
   said sample in said carrier gas is transferred via a heated transfer line into a supersonic nozzle; and
   compounds in said sample expand from said supersonic nozzle into a vacuum system while forming a supersonic molecular beam with vibrationally cold sample molecules which are ionized in said supersonic molecular beams with electrons in a fly through electron ionization ion source followed by mass analysis, ion detection and data analysis of the data obtained from the resulting mass spectral information, for identifying and/or quantifying the chemical content of said sample.

3. The method according to claim 1 wherein said capillary column is freely inserted into said heated metal tube in such a way that both ends of said capillary column protrude from said heated metal tube.

4. The method according to claim 1, including removing the column and inserting a replacement column without replacing the heated metal tube.

5. The method according to claim 1, wherein, during use, said gas chromatograph oven is heated to a temperature similar to that of the detector transfer line so that said gas chromatograph oven serves as a portion of transfer lines of said fast gas chromatograph from the injector and to the detector.

6. The method according to claim 1, wherein said carrier gas flow rate is above 4 ml/min.

7. The method according to claim 1, wherein said capillary column length is below 4 meters.

8. The method according to claim 1, wherein the full analysis cycle time is achieved in under one minute.

9. The method according to claim 1, wherein said capillary column extends from both input and output ends of said heating metal tube.

10. The method according to claim 1, wherein said capillary column is cut from a standard length capillary column without its assembly on a mounting tool or bundling with a heater and/or insulation material.

11. The method according to claim 1, wherein said resistively heated metal tube is located and mounted on top of a standard gas chromatograph oven.

12. The method according to claim 1, wherein said resistively heated metal tube is located in an enclosure and said enclosure further includes a time-programmable air cooling fan.

13. The method according to claim 1, wherein said resistively heated metal tube is interfaced with said gas chromatograph oven in a way to minimize temporary cold spots and hot spots.

14. The method according to claim 1, wherein the fast gas chromatograph is an accessory for the conversion of a standard gas chromatograph into a fast gas chromatograph as an add-on device without the removal of any substantial component from the standard gas chromatograph.

15. The method according to claim 1, wherein said injector is an Open Probe.

16. The method according to claim 1, wherein said fast gas chromatograph serves as a second dimension fast gas chromatograph of a comprehensive GC×GC or two dimensional GC-GC.

17. The method according to claim 1, wherein said sample is introduced into said gas chromatograph injector from the output of a liquid chromatograph for obtaining fast comprehensive LC×GC and/or LC×GC-MS.

18. The method according to claim 1, wherein said capillary column end is connected in a T connected with another capillary column and transfer line for enabling fast switching between standard gas chromatography analysis and fast gas chromatography analysis without a change of hardware.

19. A fast gas chromatograph device for obtaining fast gas chromatography analysis, said device comprising:
- a gas chromatograph injector;
- a gas chromatograph detector
- a capillary gas chromatography column;
- a connector for flexibly connecting said capillary column with said gas chromatograph injector;
- a source of carrier gas flow for the transferring of sample vapor in said injector into said capillary column;
- a metal tube having opposing input and output ends that is adapted to be resistively heated and that is located mostly outside a gas chromatograph oven and that is coupled via a flexible capillary column to said gas chromatograph injector and detector;
- a transfer line with a connector for flexibly connecting said flexible capillary column to a gas chromatograph detector;
- said input and output ends of said metal tube being located near a hole in the gas chromatograph oven body so that a substantial portion of said column in said metal tube is located outside said gas chromatograph oven;
- means for coupling a power supply to both ends of said metal tube for its resistive heating; and
- a controller configured for resistively heating said metal tube in a time programmed manner to facilitate fast temperature program of said capillary column in said heated metal tube, wherein the capillary column and the resistively heated metal tube are configured to provide for changing the capillary column without detaching and changing the resistively heated metal tube.

20. The device according to claim 19, further comprising a supersonic nozzle for the formation a supersonic molecular beam with vibrationally cold sample molecules which are ionized in said supersonic molecular beams by electrons in a fly through electron ionization ion source.

21. The device according to claim 19 wherein said heated metal tube enables free insertion of said capillary column into it in such a way that both ends of said capillary column are hanged out from said metal tube.

22. The device according to claim 19, further comprising means for gas chromatography capillary column replacement without the replacement of said metal tube.

23. The device according to claim 19, wherein during use said gas chromatograph oven is heated to a temperature substantially similar to that of the detector transfer line so that said gas chromatograph oven is adapted to serve as a portion of transfer lines of said fast gas chromatograph from the injector and to the detector.

24. The device according to claim 19, further comprising means for the provision of carrier gas flow rate above 4 ml/min.

25. The device according to claim 19, wherein said capillary column length is below 4 meters.

26. The device according to claim 19, wherein the full analysis cycle time can be achieved in under one minute.

27. The device according to claim 19, wherein said capillary column extends before and after said heating metal tube.

28. The device according to claim 19, wherein said capillary column is cut from a standard length gas chromatography capillary column without its assembly on a mounting tool or bundling with a heater and/or insulation material.

29. The device according to claim 19, wherein said metal tube is located and mounted on top of a standard gas chromatograph oven.

30. The device according to claim 19, further comprising an enclosure with an air cooling fan.

31. The device according to claim 19, further comprising means for minimizing thermal cold spots and hot spots near an interface of said flexible capillary column and said metal tube.

32. The device according to claim 19, wherein the fast gas chromatograph device further comprises means for the conversion of a standard gas chromatograph into a fast gas chromatograph without the removal of any substantial component from the standard gas chromatograph.

33. The device according to claim 19, wherein the gas chromatograph injector comprises an open probe.

34. The device according to claim 19, further comprising means for using said fast gas chromatograph as a second dimension fast gas chromatograph of a comprehensive GC×GC or two dimensional GC-GC.

35. The device according to claim 19, further comprising a liquid chromatograph for the introduction of its eluted sample into said gas chromatograph injector for obtaining fast comprehensive LC×GC and/or LC×GC-MS.

36. The device according to claim 19, further comprising a T-connector for the simultaneous connection of said capillary column with another capillary column for enabling fast switching between standard gas chromatography analysis and fast gas chromatography analysis without a change of hardware.

* * * * *